United States Patent [19]

Bonfield et al.

[11] 4,155,933
[45] May 22, 1979

[54] PROCESS FOR HALOGENATION OF ALDEHYDES AND PRODUCTION OF OXIMES THEREFROM

[75] Inventors: John H. Bonfield, Basking Ridge; Andiappan K. Murthy, Lake Hiawatha; Donald Pickens, Mendham, all of N.J.

[73] Assignee: Allied Chemical Corporation, Morris Township, Morris County, N.J.

[21] Appl. No.: 894,870

[22] Filed: Apr. 10, 1978

Related U.S. Application Data

[62] Division of Ser. No. 821,898, Aug. 4, 1977, Pat. No. 4,096,187.

[51] Int. Cl.$^2$ ............................................. C07C 131/00
[52] U.S. Cl. ............................ 260/566 A; 260/601 R; 260/601 H
[58] Field of Search ........... 260/566 A, 601 R, 601 H

[56] References Cited
U.S. PATENT DOCUMENTS 3,873,624  3/1975  Mathew et al. ................ 260/601 H

OTHER PUBLICATIONS

Guinot et al., Compt. Rend. vol. 231, pp. 234–236 (1950).
Hagemeyer et al., "The Chemistry of Isobutyraldehyde and its Derivatives", pp. 1, 5, 10–15, 48–49, 61, 85, 87–94 (1953).

*Primary Examiner*—Gerald A. Schwartz
*Attorney, Agent, or Firm*—Alan M. Doernberg; Jay P. Friedenson

[57] ABSTRACT

In the halogenation under reflux conditions of an unhalogenated aldehyde of the formula

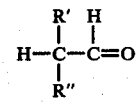

with $Cl_2$, $Br_2$ or $I_2$, the aldehyde and halogen are continuously fed into a reactor at a molar ratio of halogen to unhalogenated aldehyde between about 0.8:1 and about 1.1:1 and water is continuously fed into the unhalogenated reactor at a rate of between about 1% and about 20% by weight of aldehyde. The product α-haloaldehyde is thiohydrocarbylated and then oximated to form a 2-hydrocarbylthioaldoxime of the formula

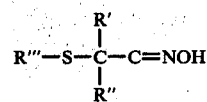

with improved yield and quality because of the improved yield and quality of unhalogenated α-haloaldehyde. An exemplary process includes the chlorination of isobutyraldehyde (IBA) to form α-chloroisobutyraldehyde (CIBA), the thiomethylation of CIBA to form 2-methyl-2 methylthio-propionaldehyde (MTIBA) and the oximation of MTIBA to form 2-methylthio-propionaldehyde oxime (aldicarb oxime or ADO).

13 Claims, No Drawings

PROCESS FOR HALOGENATION OF ALDEHYDES AND PRODUCTION OF OXIMES THEREFROM

This is a division of Application Ser. No. 821,898, filed Aug. 4, 1977, now U.S. Pat. No. 4,096,187.

BACKGROUND OF THE INVENTION

This is an improvement in the α-halogenation of aldehydes and particularly in the α-halogenation of certain aldehydes to form intermediates useful in the production of nematocides and pesticides by a process as described in U.S. Pat. Nos. 3,931,331 and 3,873,624 to Mathew et al. Briefly, the above patents describe a process for preparing an α-formyl sulfide comprising reacting under reflux conditions a halogen which is chlorine, bromine or iodine with an aldehyde of the formula

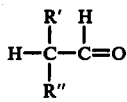

to form an α-haloaldehyde of the formula

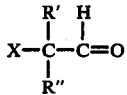

The α-haloaldehyde is subsequently reacted with a thiol salt of the formula R′″ SM to form an α-formyl sulfide of the formula

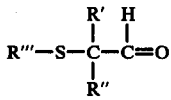

The α-formyl sulfide may then be oximated to form a 2-hydrocarbylthioaldoxime of the formula

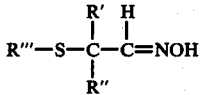

Exemplary of the process is (a) the chlorination with chlorine gas of isobutyraldehyde (hereinafter called IBA) to α-chloroisobutyraldehyde (hereinafter called CIBA); (b) the thiomethylation of CIBA with sodium thiomethylate to 2-methyl-2-methylthioisopropionaldehyde (MTIBA), (c) the oximation with hydroxylamine sulfate and ammonia to 2-methyl-2-methylthiopropionaldoxime (aldicarb oxime or ADO). These two patents are incorporated herein by reference for a fuller discussion of the process including an identification of R′, R″, R′″ and M.

The present invention is directly concerned with the first step of the above sequence for certain aldehydes, but also relates to subsequent steps insofar as the improvement in the first step provides a better quality reactant therefore and improves the overall yield. In particular, the product of the improved process of the present invention contains a reduced impurity level of homopolymers of the aldehyde and copolymers of the aldehyde and the α-haloaldehyde. The deleterious effects of these impurities was not hitherto realized. With the preferred conversion of IBA to CIBA, the level of the cyclic homopolymer impurity $(IBA)_3$ and the cyclic copolymers $(IBA)_2(CIBA)_1$ and $(IBA)_1(CIBA)_2$ particularly are reduced. Such oligomers, as well as homopolymers of α-haloaldehydes such as $(CIBA)_3$ (the latter being recognized in the above patents), are detrimental in subsequent steps because they are generally inert to the thiomethylation. Accordingly, the yield of α-formyl sulfide such as MTIBA is reduced. Furthermore, the oligomers break down during purification of the MTIBA as by distillation to form free IBA and CIBA. The free CIBA in turn is hydrolyzed during the oximation step to produce free chloride which then can cause corrosion of the stainless steel equipment preferrably used for oximation and subsequent stripping, disposal and distillation steps.

BRIEF DESCRIPTION OF THE INVENTION

The present invention includes an improvement in the halogenation under reflux conditions of an aldehyde of the formula

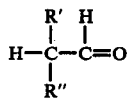

with a halogenating agent selected from the group consisting of $Cl_2$ $Br_2$ and $I_2$ to form an α-haloaldehyde of the formula

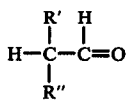

where X is Cl, Br or I and R′ and R″ independently are alkyl of 1 to 4 carbons. In the improvement, the aldehyde and halogenating agent are continuously fed into a reactor at a molar ratio of halogenating agent to aldehyde of between about 0.8:1 and about 1.1:1 and water is continuously fed into the reactor at a rate of between about 1% and about 20%, by weight of aldehyde fed. The preferred halogenating agent is $Cl_2$. The preferred aldehyde is isobutyraldehyde. The above molar ratio is preferrably between about 0.95 and about 1.0. The feed rate of water is preferrably between about 2% and 10% by weight of aldehyde.

The invention also includes an improvement in a process of preparing a 2-hydrocarbylthioaldoxime of the formula

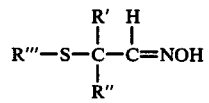

where R′ and R″ are as defined above and where R′″ is a hydrocarbon radical of 1 to 18 carbon atoms selected from the group consisting of alkyl, cycloalkyl, alkenyl, cycloalkenyl and aryl or a substituted hydrocarbon radical of the above group, said process being of the type including the halogenation under reflux conditions of an unhalogenated aldehyde of the formula

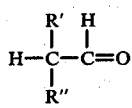

with a halogenating agent selected from Cl$_2$, Br$_2$ and I$_2$, to form an α-haloaldehyde of the formula

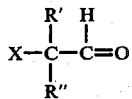

where X is Cl, Br or I and R' and R'' are as defined above, and the thiohydrocarbylation, e.g., thioalkylation of said α-haloaldehyde with a thiol salt of the formula R'''SM, where R''' is as defined above and M is an alkai or alkaline earth metal to form an α-formyl sulfide of the formula

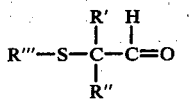

and the oximation of the said α-formyl sulfide to form said 2-hydrocarbylthioaldoxime. In the improvement, the thiohydrocarbylation, e.g., thiomethylation step includes reacting an α-haloaldehyde having less than about 1% by weight of polymers including unreacted unhalogenated. Preferably, the halogenation under reflux conditions of the unhalogenated comprises continuously feeding the unhalogenated and halogenating agent into a reactor at a molar ratio of halogenating agent to unhalogenated of between about 0.8:1 and about 1.1:1 and continuously feeding water into the reactor at a rate of between about 1% and about 20%, by weight of unhalogenated.

DETAILED DESCRIPTION OF THE INVENTION

For convenience, the following discussion will be phrased in terms of the chlorination of isobutyraldehyde (IBA) to α-chloroisobutyraldehyde (CIBA) and the subsequent thiomethylation to 2-methyl-2-methylthio-propionaldehyde (MTIBA) and oximation to 2-methyl-2-methylthio-propionaldoxime (Aldicarb oxime or ADO). It should be appreciated that the description is generally applicable to the halogenation, thiohydrocarbylation, e.g., thioalkylation and oximation of compounds as described above except where stated otherwise.

The chlorination of IBA is conducted in a reactor equipped for reflux and having inlets for continuous feed of water, IBA and chlorine and outlets for continuous withdrawal of aqueous phase, CIBA and vent gases. By "reactor" is meant any vessel, conduit portion, mixing space or the like where the appropriate feeds may mix and react. Although the preferred processes are non-catalytic, the presence of a catalyst is not intended to be excluded, especially for aldehydes of the above formula other than IBA. Water and IBA inlets are preferably lines having metered pumps for controlling the flow rate to the desired portion of between about 1% and about 20% water by weight of IBA. The preferred rate of water feed is between about 2% and about 10% water, by weight of IBA or of any aldehyde within the class specified, and the most preferred rate of water feed is about 5% of the aldehyde feed. The halogen inlet is a dip tube for chlorine gas, but may also be a liquid line with a metered pump for iodine or bromine. The halogen inlet is equipped with a metering device such as a flowmeter that ensures that the halogen: aldehyde molar ratio is between about 0.8:1 and about 1.1:1, with a preferred molar ratio between about 0.95:1 and about 1.0:1.

The molar ratio of halogen:aldehyde has been found to be critical because, if the halogen rate is deficient compared to the above ranges, a substantial proportion of unreacted aldehyde will accumulate in the α-haloaldehyde product. It should be appreciate that both the aldehyde and the α-haloaldehyde form oligomers such as trimers which will be present in the α-haloaldehyde product stream withdrawn from the reactor. In the conversion of IBA to CIBA, such oligomers are predominantly the homopolymers (CIBA)$_3$ and (IBA)$_3$ and the copolymers (CIBA)$_2$(IBA)$_1$ and (CIBA)$_1$(IBA)$_2$. It is believed that IBA readily and reversibly converts under reaction conditions to (IBA)$_3$, which converts quickly to (CIBA)$_1$(IBA)$_2$ in the presence of CIBA and that (CIBA)$_1$(IBA)$_2$ converts slowly to (CIBA)$_2$(IBA)$_1$ in the presence of free CIBA. It is not believed that (CIBA)$_2$(IBA)$_1$ converts to (CIBA)$_3$ at any appreciable rate. It also appear that (IBA)$_3$ both forms from and decomposes into free IBA at reaction temperatures at a far greater rate than either copolymer or (CIBA)$_3$. The presence of (IBA)$_3$ and especially of the copolymers detracts from the quality of chlorination product. Furthermore, as discussed below, when the present halogenation process is the first step of a process for forming a 2-hydrocarbylthioaldoxime, than the presence of homopolymers and particularly copolymers in the halogenation product detracts from overall yields and quality in two ways. First a portion of the initial aldehyde is not halogenated and thus cannot form the desired product. It may however consume other reactants, and especially the hydroxylamine source. Second, in the copolymers that form, a portion of the α-haloaldehyde is tied up during thioalkylation such that it is not thiomethylated to any substantial degree.

For example, if three percent of the IBA feed does not react but instead forms (IBA)$_3$ which converts to (CIBA)$_1$(IBA)$_2$ and to (CIBA)$_2$(IBA), and all of the freed IBA reforms copolymers, then the yield of free CIBA is not merely reduced by 3%, but rather by 6–9%. During thiomethylation of the free CIBA, CIBA which is tied up in copolymers (and in CIBA homopolymers) is essentially inert to the sodium thiomethylate. Thus when MTIBA is recovered from the thiomethylation reaction, the entire 6–9% yield loss attributable to free IBA will be seen.

If the chlorine is fed in excess compared to the above ranges, IBA is overchlorinated, as to α-chloro isobutyl chloride (CIBC or (CH$_3$)$_2$.CCl.COCl), which decomposes into 2,2-dichloropropane. A very minor amount of overchlorination CIBC is almost unavoidable. Nevertheless, the presence of over about 1–2% 2,2-dichloropropane in the CIBA product stream or vent gases is indicative of an excess chlorine feed.

The presence of water fed into the reaction mixture surprisingly increases the conversion to CIBA even more. With the preferred 2–10% water by volume of IBA, the free IBA in the reaction mass drops to below 1%. Furthermore, when the CIBA product stream is distilled, the residue remaining (including trimers, higher oligomers and products of various minor side reactions) is reduced materially such that yield of CIBA after distillation based on IBA feed is 95% or better. Formation of (IBA)$_3$ and the copolymers (CIBA)$_1$-(IBA)$_2$ and (CIBA)$_2$(IBA)$_1$ is greatly diminished. Although the present invention is not tied to any theory, it is postulated that the presence of water within the above range directly, or indirectly by first reacting with chlorine helps stabilized enolization of IBA into the transient species (CH$_3$)$_2$.C=OH with which Cl$_2$ may then react to form H$^+$, Cl$^-$ and CIBA. An excess of water, as for example about 100% by weight of IBA, appears to promote overchlorination to CIBC.

The precise residence time is not critical subject to the following minimums. The size of the reactor and IBA feed rate are preferably adjusted to minimize the free IBA concentration in the reaction mass, preferably to below about 3% and more preferably to below about 1%. A minimum residence time of about 3.0 hours or more is generally required, with about 3.5–4.0 hours being preferred. By "residence time" is meant reaction volume/IBA feed rate. It is also preferred that the reflux pass into a trap from which the aqueous layer containing predominantly water and byproduct HCl can be withdrawn, with the condensed organic layer containing CIBA predominantly returned to the reaction mass.

The temperature and pressure of the halogenation reaction are not critical, although reflux conditions are required. In general, substantially atmospheric pressures and temperatures of about 35° to 80° C. are preferred, with about 70°–75° C. being more preferred.

Homopolymers of CIBA may also form in the reaction mass, in the product CIBA stream or in the CIBA distillation column. Generally, conversion of CIBA to (CIBA)$_3$ and the like is much slower than polymerization of IBA and, accordingly, (CIBA)$_3$ formation in the reactor and product CIBA stream is generally below about 1%. Later formation of (CIBA)$_3$ can be minimized by storing CIBA for the least possible time before thiomethylation and, even then, storing at 60°–90° C. where polymerization into (CIBA)$_3$ occurs less freely than at lower temperatures. Distilling off lites and degassifying dissolved HCl from the CIBA (since HCl catalyzes polymerization) also reduces (CIBA)$_3$ formation. The lites distillation is preferably conducted as the product stream is withdrawn so as to remove HCl.

The CIBA output may thus be degassed with N$_2$ or the like, preferably on a continual basis until the CIBA is further reacted.

As indicated above, the CIBA product stream is distilled twice to remove first lites such as HCl and 2,2-dichloropropane and then the CIBA from residues which include most of the polymers formed. The CIBA recovered is then degassed or sparged and stored at about 60°–90° C. before thiomethylation. It is then thiomethylated with an aqueous solution of sodium thomethylate (made by absorbing methyl mercaptan in aqueous sodium hydroxide solution as, for example, 25–28 weight% sodium thiomethylate made from 20 weight sodium hydroxide). Thiomethylation is preferably conducted at between about −30° C. and 40° C. The product MTIBA is then decanted from an aqueous brine containing byproduct NaCl and then fractionated at atmospheric pressure to remove lites and subsequently at reduced pressure to recover MTIBA from residues.

It should be appreciated that various polymers, including especially the copolymers (CIBA)$_1$(IBA)$_2$ and (CIBA)$_2$(IBA)$_1$, are present in the crude CIBA stream, but will in large part remain with the residues after the CIBA is distilled off. A substantial proportion, however, of the copolymers will reform in the CIBA distillate, particularly if free IBA is present and the material is held for any significant time. They remain unreacted in the thiomethylation step but break down to IBA and CIBA under distillation both at atmospheric pressure and at reduced pressure in final recovery. According, if over about 1% of the crude CIBA stream is such copolymers, they may be present in the final MTIBA stream at concentrations of about 500–10,000 ppm.

The MTIBA is then oximated with hydroxylamine or a hydroxylamine source. In the preferred process, a hydroxylamine salt such a hydroxylamine sulfate is combined with a base such as ammonia to oximate MTIBA to ADO and coproduce ammonium sulfate. The oximation may occur at about 50°–100° C. (for example 90° C.) and at a pH of between about 3.5 and 8 (preferably between about 5 and 6). The product 2-hydrocarbylthioaldoxime, which is ADO when IBA is the initial aldehyde and sodium thiomethylate is the thioalkylation reagent, may then be separated as an organic phase from water and other byproducts and vacuum distilled. Using hydroxylamine sulfate and ammonia as the hydroxylamine source, the byproduct ammonium sulfate is present in the aqueous layer. It is often desired to recover this ammonium sulfate for fertilizer or other uses in order to make the entire process economical.

Copolymers introduced with MTIBA into the oximation reaction mixture will, for the most part, decompose into monomer aldehydes and α-haloaldehydes. The free α-haloaldehydes will quickly hydrolyze to form free halide (i.e. chloride). This effect, which may occur earlier to a lesser extent during MTIBA distillation, forms a chloride which may be found in the aqueous phase with the ammonium sulfate. In practice, the presence of free halide interferes with the various distillation steps by precluding the use of stainless steel vesels and the like for MTIBA storage, oximation, stripping or residual organics from the ammonium sulfate aqueous phase, purification of the sulfate (generally by evaporative crystallization) and (vacuum) distillation purification of the ADO. Expensive alloys must be used because of the threat of chloride stress corrosion of stainless steel and the like.

In the formula for the aldehyde starting material, R' and R" have been limited to alkyl of 1–4 carbons because it is primarily these aldehydes among the broader group disclosed in the Mathews et al. patents that are likely to trimerize significantly during reaction. Within the claimed group, the expected trimerization, and hence the expected improvement by the present process, should be greatest where R' and R" are both methyl, ethyl or propyl and least when one especially both are isopropyl, butyl, isobutyl or tertiary butyl. Where R' and/or R" are hydrogen, halogenation may result in at least a fraction of acyl halide rather than α-haloaldehyde.

It should thus be appreciated that the present process is directed to process improvements resulting in greatly increased halogenation yield, which in the overall process, increases the yield and quality of the intermediates and product oxime to a still greater extent. The invention is illustrated in the following non-limiting examples, with comparative examples being interposed in order to show the advantages of the present invention.

COMPARATIVE EXAMPLE 1

Batch Chlorination of IBA

To 1000 grams isobutyraldehyde (IBA) contained in a stirred jacketted reactor at 25° C. equipped with refrigerated reflux condenser, chlorine gas addition was started via a sparge tube at such a rate that 850 grams (the stoichiometric amount) will have been added over a 4 hour period. There was an initial immediate exotherm temperature rise to 60°-65° C., whereupon the IBA mass started to boil. When about 10% of the above chlorine was added, the jacket temperature was gradually raised so as to maintain gentle reflux. As CIBA built in reaction mass, reaction temperature to do this gradually climbed to 69°-75° C. When 65% of stoichiometric chlorine had been added, the reaction mass became slightly green and free IBA content by analysis was about 5%; (IBA)$_3$ however was appreciable. When 80-85% of stoichiometric chlorine was added, the vent gas now became green in color. If 85% of the stoichiometric chlorine was then exceeded, residual IBA at 3% of reaction mass was not further diminished, CIBA content started to decrease and overchlorination to α-chloro-isobutyrl chloride (CIBC) started to occur. CIBA was then recovered by distillation at 125° C. and 150 absolute millimeters of mercury resulting in the recovery of 650 grams of CIBA (46% of reaction mass) which contains 5% IBA. Net CIBA was thus 617.5 grams or a yield of 41.75% based on IBA used. 760 grams of residue were left (54% of reaction mass).

COMPARATIVE EXAMPLE 2

Continuous Chlorination of IBA

The process was carried out as in Comparative Example 1 to the point where 850 grams of chlorine had been added. At this point, continuous IBA feed was started at a rate of 250 grams per hour (to a reactor holding 1000 grams), and the chlorine feed rate increased to 237 grams per hour. During the progress of this run, as the initial residue content due to the batch reaction in comparative example 1 was purged out, the % of reaction mass recoverable as CIBA gradually increased from 46% lining out at about 90%. Residue content progressively diminished from 54% of reaction mass to about 10%. Recovered CIBA showed 3% free IBA on immediate analysis. At this point, for every 250 grams IBA and 237 grams chlorine fed, 365 grams reactor effluent were obtained which yielded 329 grams of CIBA recovered by distillation which contained 3% IBA. Net recovered CIBA is thus 318 grams which is 86% yield on IBA fed.

EXAMPLE 3

Continuous Chlorination of IBA With Water Feed

The procedure of comparative example 2 was continued and 12.5 grams/hour of water (5 weight % of the IBA feed) were then fed to the reactor. An aqueous concentrated HCl phase started to decant out from the reactor reflux in a trap provided. The continuously withdrawn reaction mass as above resulted in about 95% being recoverable as CIBA with now negligible IBA content and only 5% of the total mass appearing as residue. Reactor effluent was still 365 grams/hour compared to 250 grams/hour of IBA fed. Recoverable CIBA, was now 347 grams/hour, leaving only 18 grams/hour of residue. The 347 grams were essentially pure CIBA and the CIBA yield was 94% relative to IBA fed on a molar basis.

COMPARATIVE EXAMPLE 4

A CIBA product fraction was recovered by distillation from a batch chlorination as in comparative example 1 but scaled up by a factor of 3.0-3.5. A portion of this fraction was held for two hours before distillation. The IBA content of 4-5% is shown on Table 1. The presence of IBA in the CIBA results in losses to trimer in excess of the % of the IBA present.

COMPARATIVE EXAMPLE 5

Thiomethylation of CIBA

The α-chloro isobutyraldehyde products of comparative Example 4 and of Example 3, also scaled up by a factor of between about 3.0 and 3.5, were converted to 2-methyl-2-methylthiopropionaldehyde (MTIBA) by the following procedure. To 200 grams of 20 wt. % aqueous sodium hydroxide solution was added with agitation and by gas sparge 48 grams of methyl mercaptan at 25°-30° C. This produced 248 grams 23.2 wt. % aqueous CH$_3$S Na solution. To this solution was then added 106.5 grams α-chloro isobutyraldehyde slowly with good agitation and cooling to hold at 30°-40° C. The mixture was then allowed to phase separate yielding 118 grams crude MTIBA and 226.5 grams 25.8 wt. % sodium chloride brine. Chloride content of the MTIBA was assayed by combustion (O$_2$) over aqueous NaOH solution which was then acidified with HNO$_3$ and potentionetrically titrated against standard AgNO$_3$ solution to a specified end point. For the three cases, the chloride content of the crude MTIBA was analyzed as shown in Table 1.

TABLE I

| Run | CIBA from Example | IBA Content | Period CIBA Stored | ppm Chloride |
|---|---|---|---|---|
| A | 4 | 4-5% | 2 hr. | 30,500 |
| B | 4 | 4-5% | 0 | 15,000 |
| C | 3 | 1% | 0 | 9,000 |

Each crude MTIBA fraction was then continuously subjected to lites fractionation by continuous feed to the 10th plate of a 30 plate column operating at a 20:1 reflux ratio, head temperature 80° C. and reboiler temperature 140°-141° C. 5% of the feed as lites were removed. The MTIBA was then recovered from the bottoms by flash to 125° C. reboiler temperature at 100 mm mercury absolute. The final product MTIBA samples then contained chloride in the following concentration:

A    2000-3000
B    1000-1500
C    300-400

EXAMPLE 6

The three final product MTIBA samples as prepared in Example 5 were then continuously reacted with Raschig process hydroxylamine solution which had the following assay:

|  | Wt. % |
|---|---|
| H$_2$SO$_4$ | 8.17 |
| (NH$_2$OH)$_2$H$_2$SO$_4$ | 11.06 |
| (NH$_4$)$_2$SO$_4$ | 23.5 |
| NH$_4$NO$_3$ | 1.5 |

Reaction was conducted continuously in the following manner.

To a two stage agitated backmix reactor system with each stage being 2000 ml in volume and maintained at 85°–90° C. by heated jackets was fed 200 g/hr MTIBA and 1260 g/hr of the above solution. NH3 gas was introduced at a rate to hold the first stage pH at 7.5 to 8.0. This required about 65 g/hr. NH3. The second stage reaction product, after being cooled to 40°–45° C., entered a separator wherein 226 g/hr crude 2-methyl-2-methylthio propionaldehyde oxime and 1299 g/hr. 43.7% (NH4)2SO4 solution were phase separated. This solution entered a 15 plate stripper column at the top plate. With the reboiler at 103°–105° C., 5–10% of this amount was removed continuously and returned to the first stage oximator. The residue (NH4)2SO4 solution is then subject to continuous total evaporation crystallization coupled with centrifigation recovery of the sulfate. The crystallizer operates at 50°–60° C. under reduced pressure. The entire evaporation process is conducted in vessels having stainless steel walls.

The sulfate bottoms solution had the following ppm chloride levels in relation to that in the MTIBA fed as follows

|   | MTIBA Feed ppm Cl | Sulfate Bottoms ppm Cl | |
|---|---|---|---|
|   |   | Total | INorganics |
| A | 2000–3000 | 364–545 | 35–55 |
| B | 1000–1250 | 182–227 | 18–22 |
| C | 300–400 | 55–73 | 5–7 |

As can be ssen the improved operations are effective in substantially reducing such chloride levels in the sulfate phase.

The crude oxime also shows substantial reduction in chloride levels being of the order of 50, 20 and 10 ppm total chloride respectively. This product oxime is subject to dehydration by water-oxime separation at 50 mm Hg. Abs. followed by total thin film recovery of the product at 10 mm Hg. Abs.

EXAMPLE 7

Equimolar amounts of Cl2 and (CH3CH2CH2)2CHCHO or 2-propyl pentanal are continuously fed into a reactor after start-up in accordance with Example 3. Water in the amount of 8% by weight of aldehyde is also continuously fed into the reactor. Vapor from the reactor is condensed and separated into an aqueous and an organic phase with the organic phase returned as reflux and the organic phase withdrawn. The product 2-chloro, 2-propyl pentanal is withdrawn continuously with residence times long enough to keep free aldehyde concentrations below about 3%, yielding a product with reduced oligomer content.

We claim:

1. In a process for preparing a 2-hydrocarbylthioaldoxime of the formula

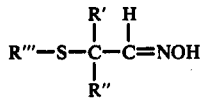

where R' and R" independently are alkyl of 1 to 4 carbons, and R''' is a hydrocarbon radical of 1 to 18 carbon atoms selected from the group consisting of alkyl, cycloalkyl, alkenyl, cycloalkenyl and aryl or a substituted hydrocarbon radical of the above group, said process comprising the halogenation under reflux conditions of an unhalogenated aldehyde of the formula

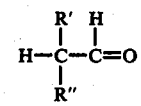

with a halogenating agent selected from Cl2, Br2 and I2, to form an α-haloaldehyde of the formula

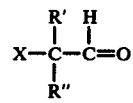

where X is Cl, Br or I and R' and R" are as defined above, and the thiohydrocarbylation of said α-haloaldehyde with a thiol salt of the formula R'''SM, where R''' is as defined above and M is an alkali or alkaline earth metal to form an α-formyl sulfide of the formula

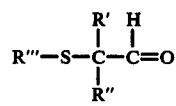

and the oximation of the said α-formyl sulfide to form said 2-hydrocarbylthioaldoxime, the improvement wherein the halogenation under reflux conditions of the unhalogenated aldehyde comprises continuously feeding the unhalogenated aldehyde and halogenating agent into a reactor at a molar ratio of halogenating agent to unhalogenated aldehyde of between about 0.8:1 and about 1.1:1 and continuously feeding water into the reactor at a rate of between about 1% and about 20% by weight of unhalogenated aldehyde and wherein the thiohydrocarbylation step includes reacting an α-haloaldehyde having less than about 1% by weight of homopolymers and copolymers of unreacted unhalogenated aldehyde.

2. The process of claim 1 wherein the halogenation agent is Cl2.

3. The process of claim 2 wherein the unhalogenated aldehyde is isobutyric aldehyde.

4. The process of claim 3 wherein the unhalogenated aldehyde and halogenating agent are fed at a molar ratio of halogenating agent to unhalogenated aldehyde of between about 0.95:1 and about 1.0:1 and water is fed at a rate of between about 2% and about 10% by weight of unhalogenated aldehyde.

5. The process of claim 2 wherein the halogenation reaction mass is sufficiently large and the unhalogenated aldehyde feed rate sufficiently small to maintain the unhalogenated aldehyde concentration of the reaction mass below about 3% by weight.

6. The process of claim 2 wherein the halogenation reaction mass is sufficiently large and the unhalogenated aldehyde feed rate sufficiently small to maintain the unhalogenated aldehyde concentration of the reaction mass below about 1% by weight.

7. The process of claim 3 wherein α-haloaldehyde being α-chloroisobutyraldehyde is continuously withdrawn from the reactor and distilled once to remove lites and a second time to distill the α-haloaldehyde from residues.

8. The process of claim 7 wherein the distilled α-haloaldehyde is then stored at between about 60° C. and about 90° C.

9. The process of claim 7 wherein the distilled α-haloaldehyde is purged of dissolved HCl by sparging with an inert gas.

10. The process of claim 7 wherein the α-formyl sulfide is distilled once to remove lites and a second time to distill α-formyl sulfide from residues.

11. The process of claim 7 wherein the oximation step comprises reacting the α-formyl sulfide with hydroxylamine sulfate and a base and recovering an aqueous sulfate salt solution.

12. The process of claim 11 wherein said base is ammonia and said aqueous salt solution is an ammonium sulfate solution.

13. The process of claim 11 wherein the reacting and recovering portions of the oximation step are conducted in stainless steel vessels.